United States Patent
Terry et al.

(10) Patent No.: US 8,652,036 B2
(45) Date of Patent: Feb. 18, 2014

(54) SPECULUM

(75) Inventors: Frederick M. Terry, Plymouth, MA (US); Dana Cote, Boxford, MA (US)

(73) Assignee: Beaver-Visitec International (US), Inc., Lake Forest, IL (US)

( * ) Notice: Subject to any disclaimer, the term of this patent is extended or adjusted under 35 U.S.C. 154(b) by 57 days.

(21) Appl. No.: 12/911,110

(22) Filed: Oct. 25, 2010

(65) Prior Publication Data

US 2011/0098538 A1     Apr. 28, 2011

Related U.S. Application Data

(60) Provisional application No. 61/254,263, filed on Oct. 23, 2009, provisional application No. 61/303,764, filed on Feb. 12, 2010.

(51) Int. Cl.
*A61B 1/32* (2006.01)
(52) U.S. Cl.
USPC .......................................... 600/236; 600/206
(58) Field of Classification Search
USPC .......................... 606/205–209; 600/184–246
See application file for complete search history.

(56) References Cited

U.S. PATENT DOCUMENTS

| | | | | | |
|---|---|---|---|---|---|
| 595,512 | A | * | 12/1897 | Anderson | 81/318 |
| 835,968 | A | * | 11/1906 | Mennes | 601/40 |
| 1,067,572 | A | * | 7/1913 | Abbott | 600/237 |
| 1,472,380 | A | * | 10/1923 | Atwood | 452/69 |
| 2,075,534 | A | * | 3/1937 | McCormack | 600/219 |
| 2,291,413 | A | * | 7/1942 | Siebrandt | 606/103 |
| 2,583,892 | A | * | 1/1952 | Shellhouse | 606/137 |
| 2,702,540 | A | * | 2/1955 | Debeh | 600/218 |
| 3,316,913 | A | * | 5/1967 | Swenson | 606/108 |
| 3,367,336 | A | * | 2/1968 | Eizenberg | 606/210 |
| 3,392,727 | A | * | 7/1968 | Hanlon | 606/210 |
| 3,616,497 | A | * | 11/1971 | Weston | 24/542 |
| 3,636,954 | A | * | 1/1972 | Weston | 606/208 |
| 3,809,094 | A | * | 5/1974 | Cook | 606/151 |
| 3,893,454 | A | * | 7/1975 | Hagelin | 600/219 |
| 3,906,957 | A | * | 9/1975 | Weston | 606/205 |
| 3,972,333 | A | * | 8/1976 | Leveen | 606/174 |
| 4,257,406 | A | * | 3/1981 | Schenk | 600/219 |
| 4,365,625 | A | * | 12/1982 | Rind | 128/207.14 |
| 4,526,172 | A | * | 7/1985 | Stephenson | 606/208 |

(Continued)

FOREIGN PATENT DOCUMENTS

| DE | 10 2006 021889 A1 | 11/2007 |
|---|---|---|
| FR | 712 704 A | 10/1931 |

(Continued)

*Primary Examiner* — Mary Hoffman
(74) *Attorney, Agent, or Firm* — Hoffmann & Baron, LLP

(57) ABSTRACT

In one aspect, a speculum is provided herein which includes a first arm having a first channel formed thereon adapted to the shape of an eyelid; a second arm having a second channel formed thereon adapted to the shape of an eyelid; a hinge unitarily formed with the first and second arms, the hinge permitting the first and second arms to selectively rotate about an axis rotation, the selective rotation causing the first and second channels to selectively move closer and farther apart; and, a position retaining arrangement. The position retaining arrangement includes a first element formed unitarily with the first arm, and a second element formed unitarily with the second arm. The first and second elements are configured to cooperatively retain the first and second arms in a selected rotational position. Advantageously, with the subject invention, a unitary speculum may be formed which includes an adjustable position retaining arrangement.

17 Claims, 23 Drawing Sheets

(56) References Cited

U.S. PATENT DOCUMENTS

| | | | | |
|---|---|---|---|---|
| 4,605,002 A | * | 8/1986 | Rebuffat | 606/148 |
| 4,754,746 A | * | 7/1988 | Cox | 600/210 |
| 5,002,561 A | * | 3/1991 | Fisher | 606/210 |
| 5,054,906 A | * | 10/1991 | Lyons, Jr. | 351/205 |
| 5,070,860 A | * | 12/1991 | Grounauer | 600/236 |
| 5,341,798 A | * | 8/1994 | Grounauer | 600/236 |
| 5,462,435 A | * | 10/1995 | Young | 433/140 |
| 5,464,413 A | * | 11/1995 | Siska et al. | 606/151 |
| 5,514,148 A | * | 5/1996 | Smith, III | 606/151 |
| 5,522,290 A | * | 6/1996 | Visser et al. | 81/427 |
| 5,556,403 A | * | 9/1996 | Michalos | 606/148 |
| 5,591,203 A | * | 1/1997 | Fahy | 606/207 |
| 5,697,933 A | * | 12/1997 | Gundlapalli et al. | 606/96 |
| 5,746,757 A | * | 5/1998 | McGuire | 606/148 |
| 5,797,919 A | * | 8/1998 | Brinson | 606/105 |
| 5,997,566 A | * | 12/1999 | Tobin | 606/205 |
| 6,159,217 A | * | 12/2000 | Robie et al. | 606/88 |
| 6,302,842 B1 | | 10/2001 | Auerbach et al. | |
| 6,440,065 B1 | * | 8/2002 | Hered | 600/236 |
| 6,544,169 B2 | * | 4/2003 | Putrino et al. | 600/236 |
| 6,635,072 B1 | * | 10/2003 | Ramamurti et al. | 606/208 |
| 7,189,234 B2 | * | 3/2007 | Zucherman et al. | 606/249 |
| 2002/0103421 A1 | * | 8/2002 | Putrino et al. | 600/236 |
| 2007/0244516 A1 | * | 10/2007 | Chiu et al. | 606/207 |
| 2008/0172085 A1 | * | 7/2008 | Chiu et al. | 606/205 |
| 2008/0177297 A1 | * | 7/2008 | Steiner et al. | 606/205 |
| 2008/0234765 A1 | * | 9/2008 | Frasier et al. | 606/86 A |
| 2009/0227846 A1 | * | 9/2009 | Beck | 600/236 |
| 2010/0331878 A1 | * | 12/2010 | Kleinwachter | 606/205 |

FOREIGN PATENT DOCUMENTS

| | | |
|---|---|---|
| RU | 2 020 860 C1 | 10/1994 |
| SU | 1 736 487 A1 | 5/1992 |
| WO | 92/18055 A1 | 1/2011 |

* cited by examiner

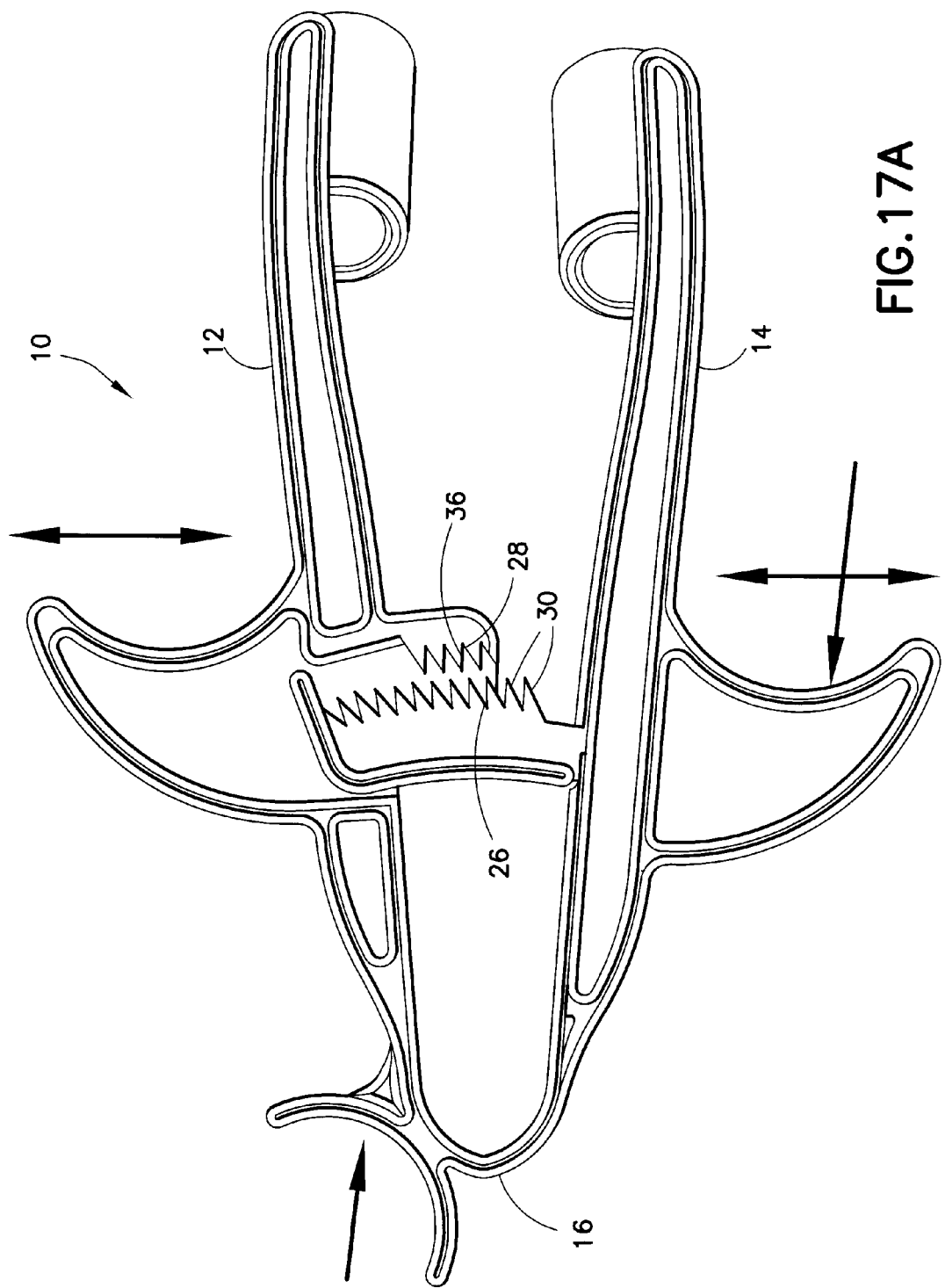

SPECULUM

CROSS-REFERENCE TO RELATED APPLICATIONS

This application claims priority to U.S. Provisional Patent Application No. 61/254,263, filed Oct. 23, 2009, and claims priority to U.S. Provisional Patent Application No. 61/303,764, filed Feb. 12, 2010, the entire contents of these applications being incorporated by reference herein.

FIELD OF THE INVENTION

This invention relates to speculums for opening, and maintaining in an open position, eyelids, and, more particular, to speculums having arrangements for being retained at specific open positions.

DESCRIPTION OF PRIOR ART

Speculums are know in the prior art for opening, and maintaining in an open position, eyelids during ocular procedures or surgery. Prior art speculums include bent-wire speculums where the speculum is formed from a unitary piece of resilient wire. The speculums are provided in unbiased, rest states, corresponding to the open position of the eyelids. For use, the speculums are compressed to engage the eyelids and, then, allowed to expand to cause opening thereof. These speculums have no provision for positional adjustment or being retained at a particular position. The inherently generated elastic force is used to maintain these speculums during use.

Speculums have been also provided in the prior art with separate positional adjustment arrangements. For example, speculums have been provided which include a bolt spanning between the arms of the speculum, wherein threaded movement of a nut along the length of the bolt causes positional adjustment of one or both of the arms. These speculums require components in addition to the speculum itself.

SUMMARY OF THE INVENTION

In one aspect, a speculum is provided herein which includes a first arm having a first channel formed thereon adapted to the shape of an eyelid; a second arm having a second channel formed thereon adapted to the shape of an eyelid; a hinge unitarily formed with the first and second arms, the hinge permitting the first and second arms to selectively rotate about an axis rotation, the selective rotation causing the first and second channels to selectively move closer and farther apart; and, a position retaining arrangement. The position retaining arrangement includes a first element formed unitarily with the first arm, and a second element formed unitarily with the second arm. The first and second elements are configured to cooperatively retain the first and second arms in a selected rotational position. Advantageously, with the subject invention, a unitary speculum may be formed which includes an adjustable position retaining arrangement.

These and other features of the invention will be better understood through a study of the following detailed description and accompanying drawings.

DETAILED DESCRIPTION OF THE DRAWINGS

Figure 1:
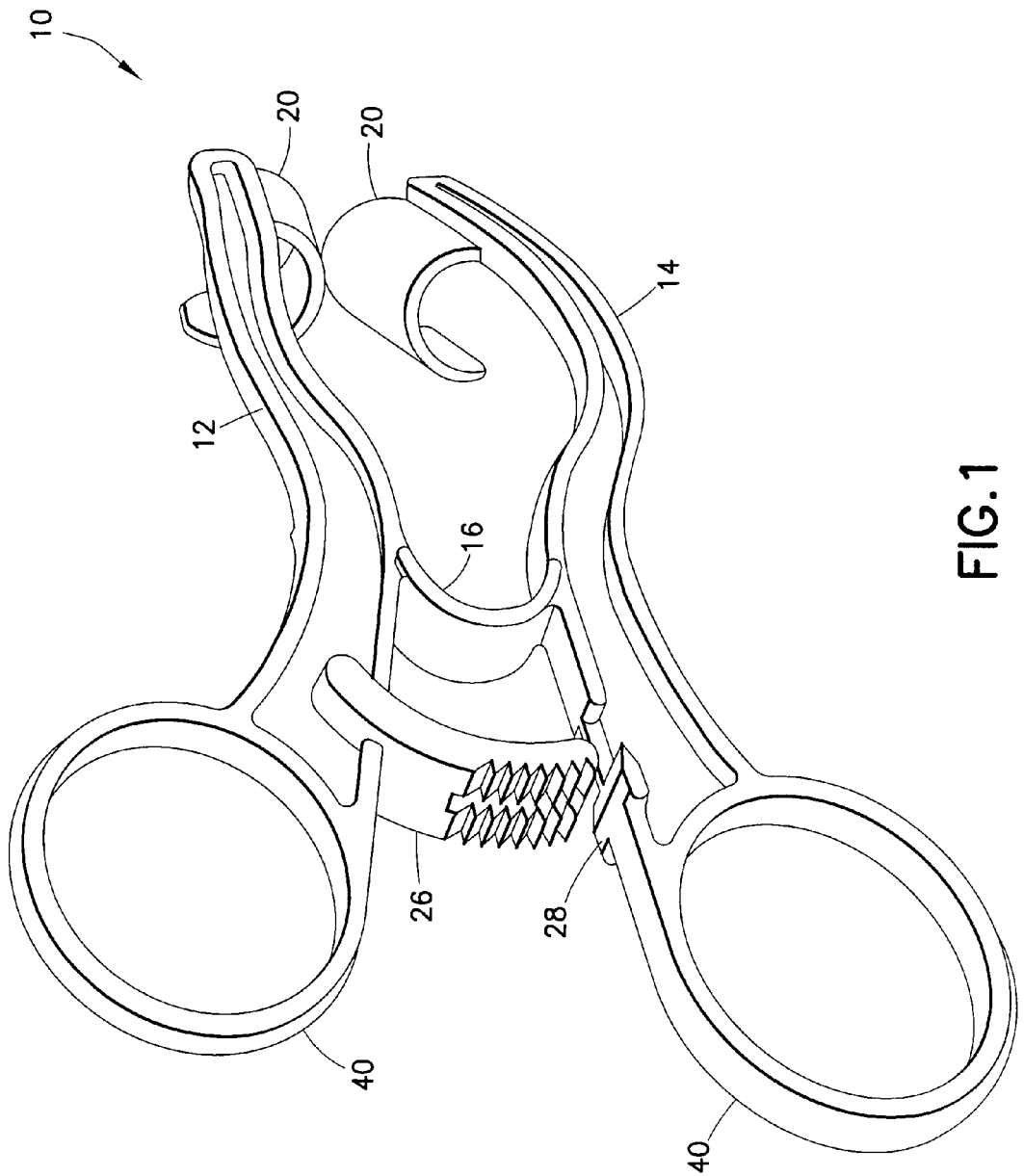
FIGS. 1-35 show a speculum, and various features thereof, formed in accordance with the subject invention.

With reference to the Figures, various embodiments of a speculum 10 are shown. The speculum 10 is useable for opening, and maintaining in an open position, eyelids during ocular procedures or surgery. Preferably, the speculum 10 is unitarily formed as one piece. In addition, it is preferred that the speculum 10 be formed from a thermoplastic material which is sterilizable. The speculum 10 is intended to be a single-use product which is sterilized, packaged for use, and discarded after use.

With reference to FIGS. 1-9, a preferred embodiment of the speculum 10 is shown. In particular, the speculum 10 includes first and second arms 12, 14 which are connected by a hinge 16. Preferably, the hinge 16 is unitarily formed with the first and second arms 12, 14. The first and second arms 12, 14 each include a distal end 18 having formed thereon a channel 20 adapted to the shape of an eyelid. The first and second arms 12, 14 each include a proximal end 22, located opposite the distal end 18. In the preferred embodiment, as shown in FIGS. 1-7, the hinge 16 is located at a mid-point of the first and second arms 12, 14 between the distal and proximal ends 18, 22.

Figure 2:
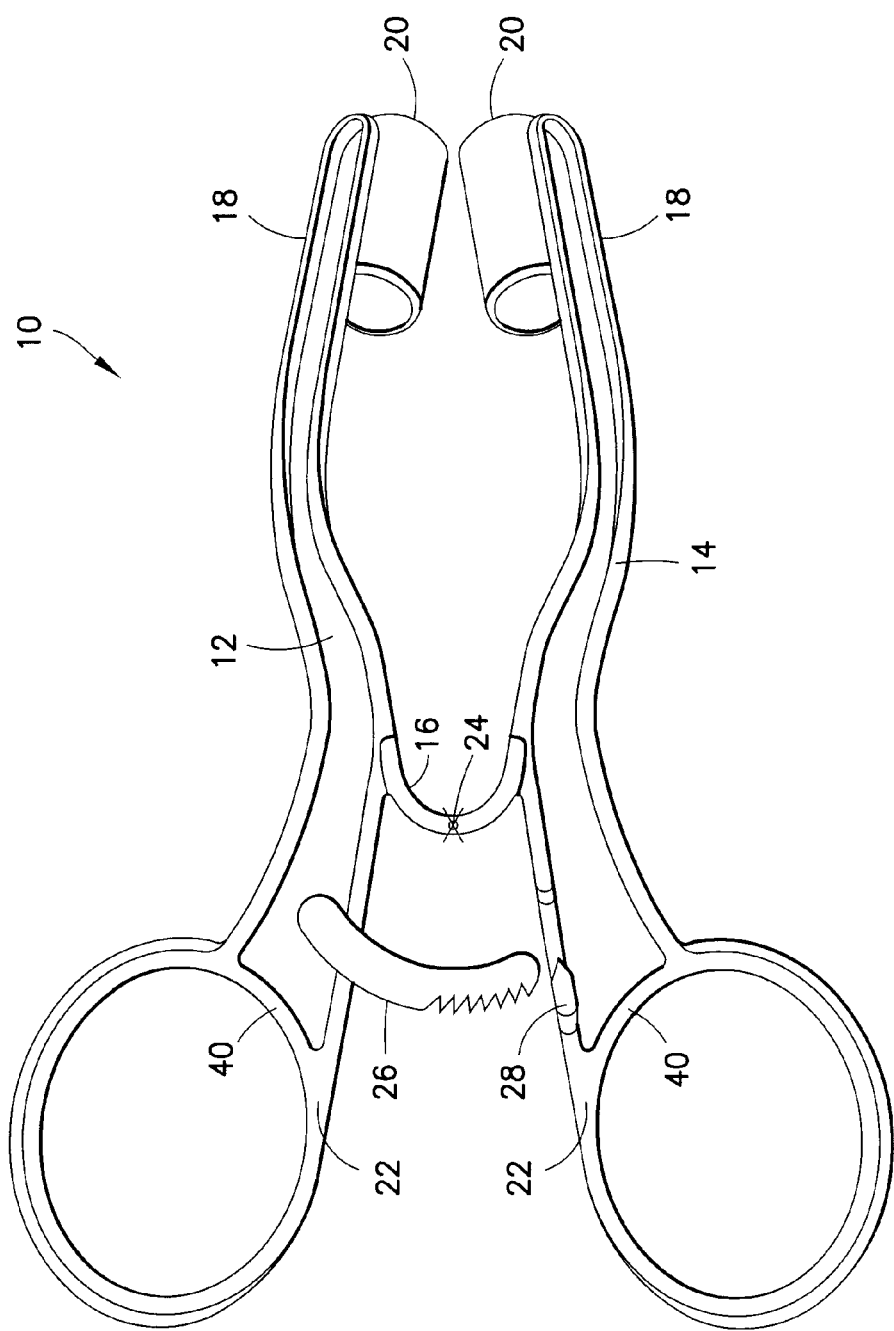
Figure 6:
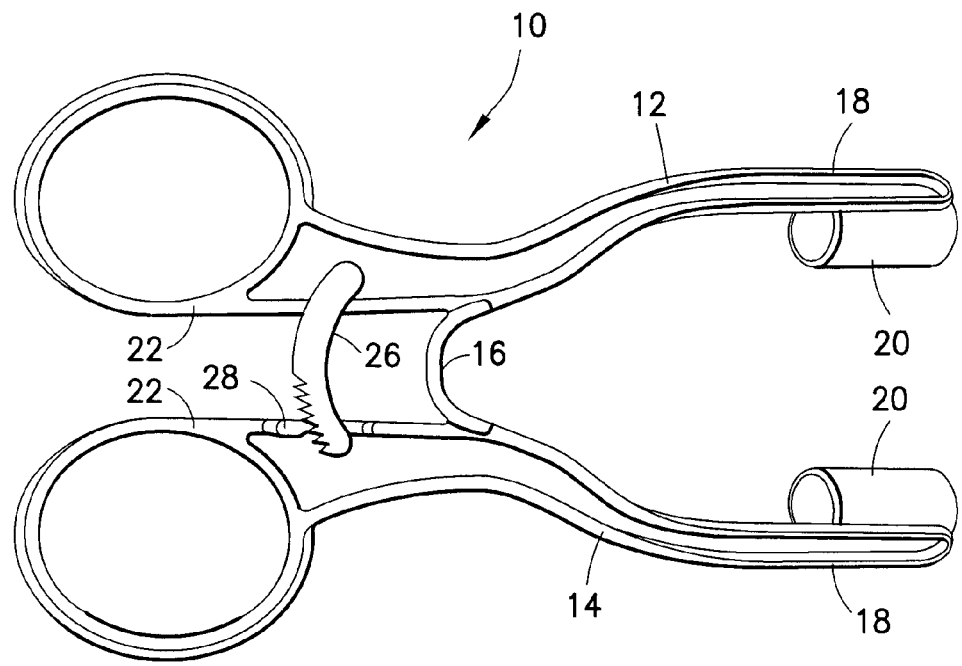
Figure 7:
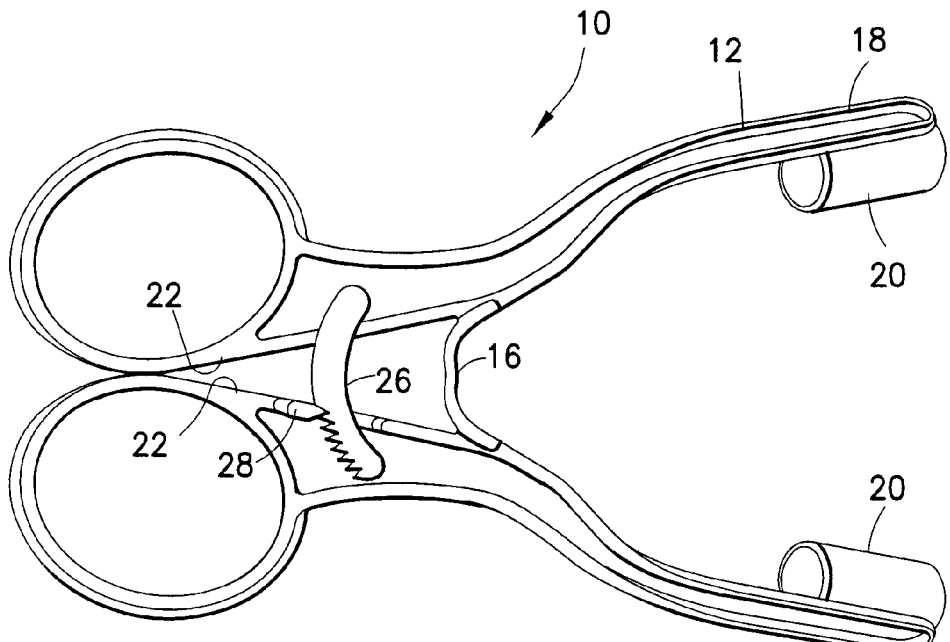

With reference to FIGS. 2, 6 and 7, movement of the proximal ends 22 of the first and second arms 12, 14 closer together, results in separation of the distal ends 18, including the channels 20, of the first and second arms 12, 14. Conversely, separation of the proximal ends 22 results in the distal ends 18, including the channels 20, coming closer together. In this manner, the first and second arms 12, 14 may be rotated about an axis of rotation, designated by reference numeral 24, to selectively cause the distal ends 18 to come closer or further apart as need be. It is preferred that in an initial state, the speculum 10 be provided in the state shown in FIG. 2, with the distal ends 18, including the channels 20, being in proximity. This state corresponds to a pre-use state. The eyelids of a patient should be engaged with the speculum 10 being in the pre-use state. With subsequent separation of the distal ends 18, as represented by FIGS. 6 and 7, a patient's eyelids may be engaged and caused to be opened to an open state, as represented by FIG. 7.

Figure 8:
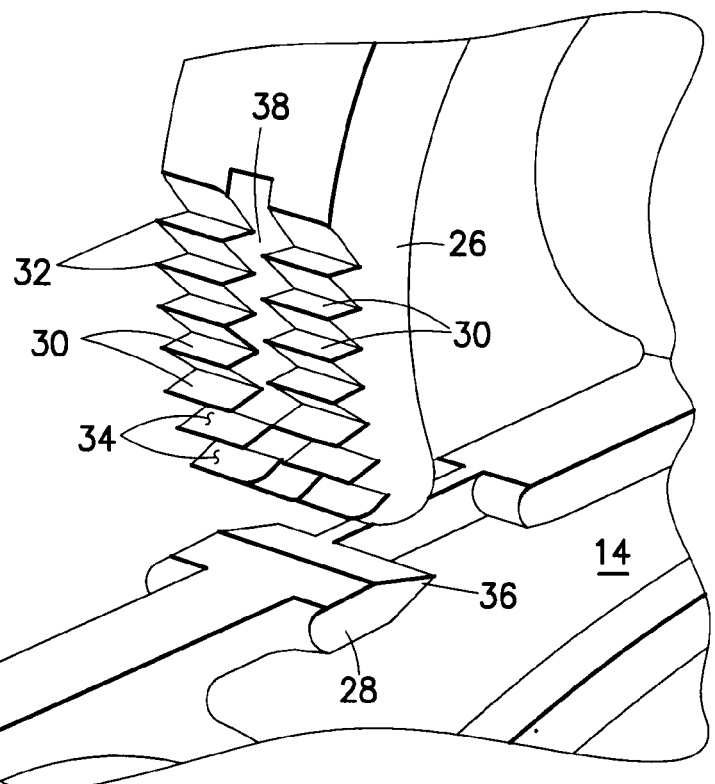
Figure 9:
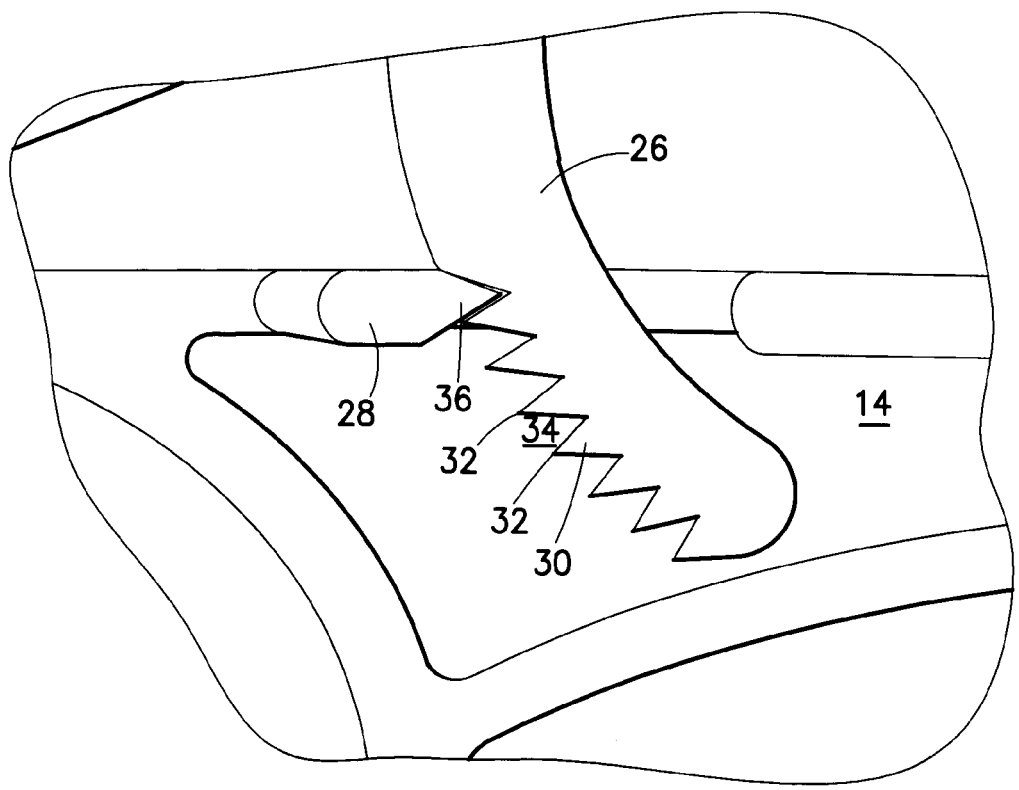
Figure 10:
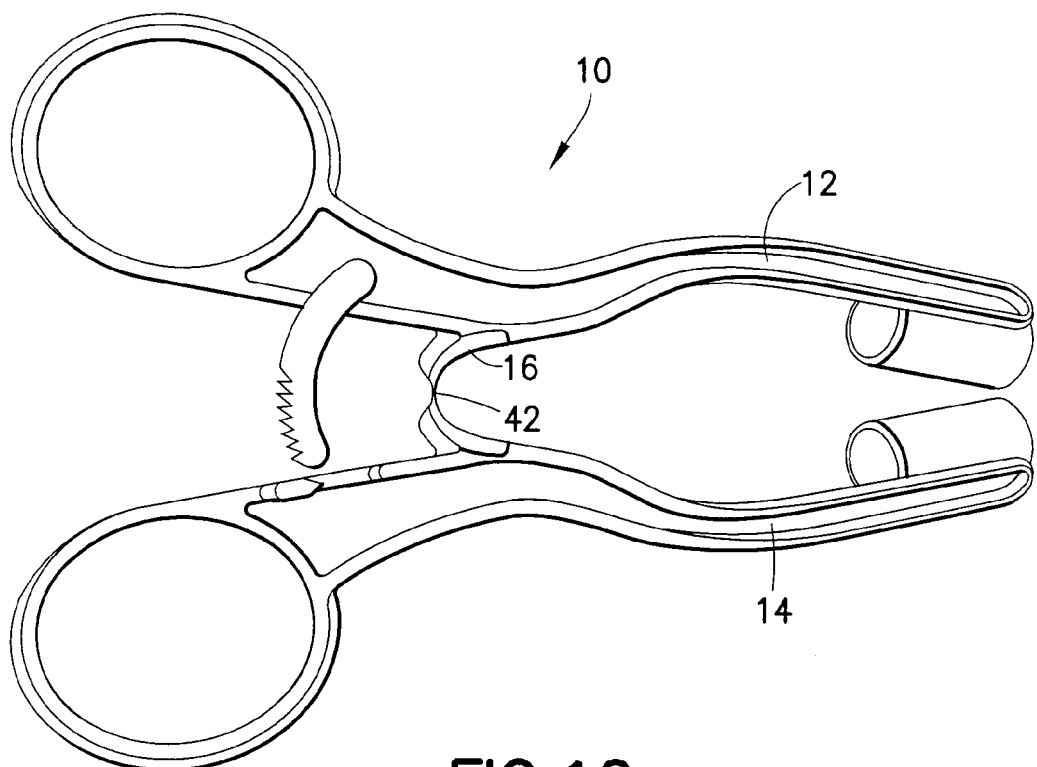
Figure 11:
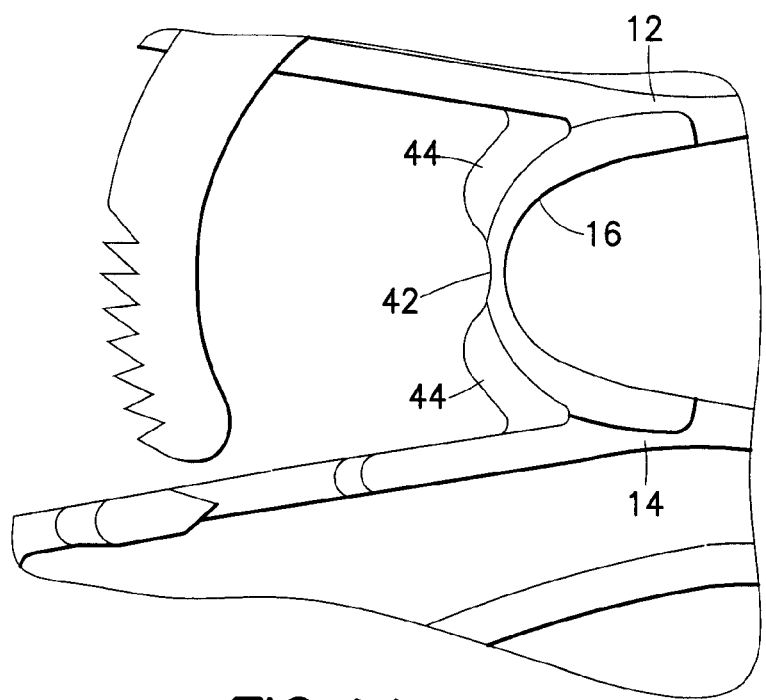
Figure 12:
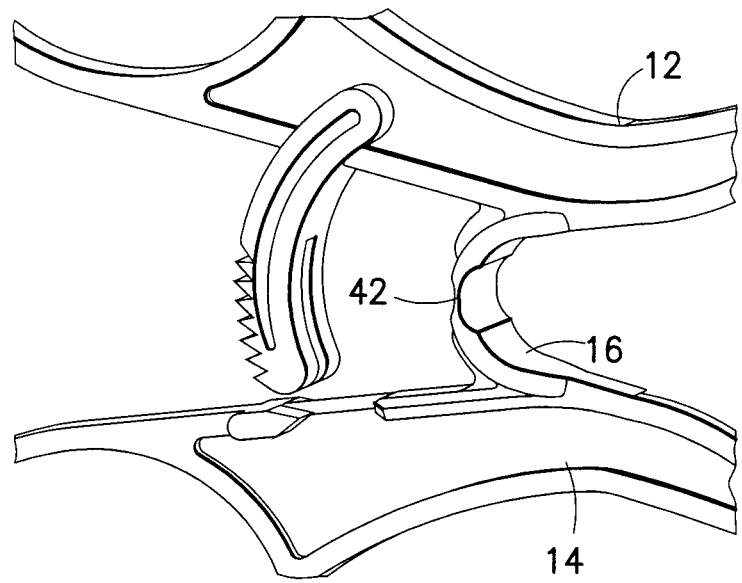
Figure 13:
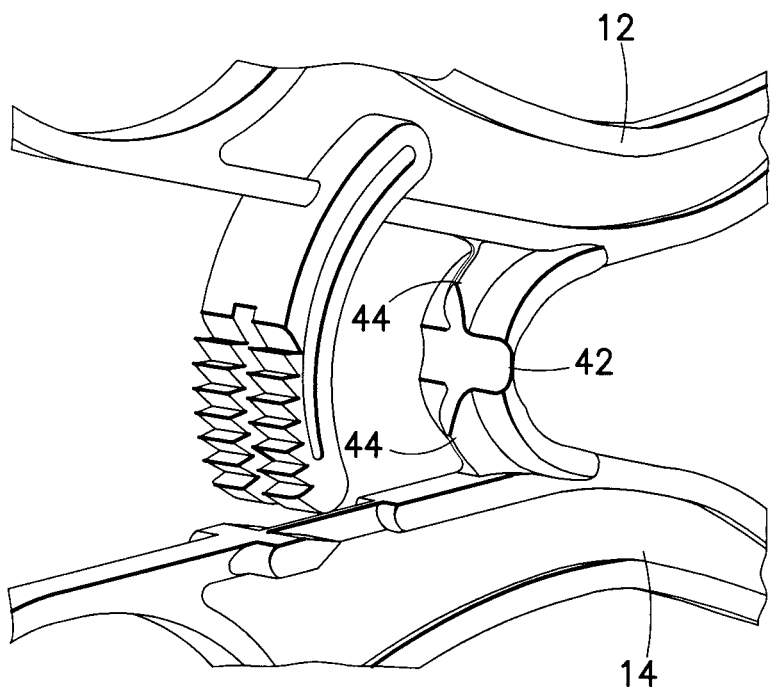
Figure 14:
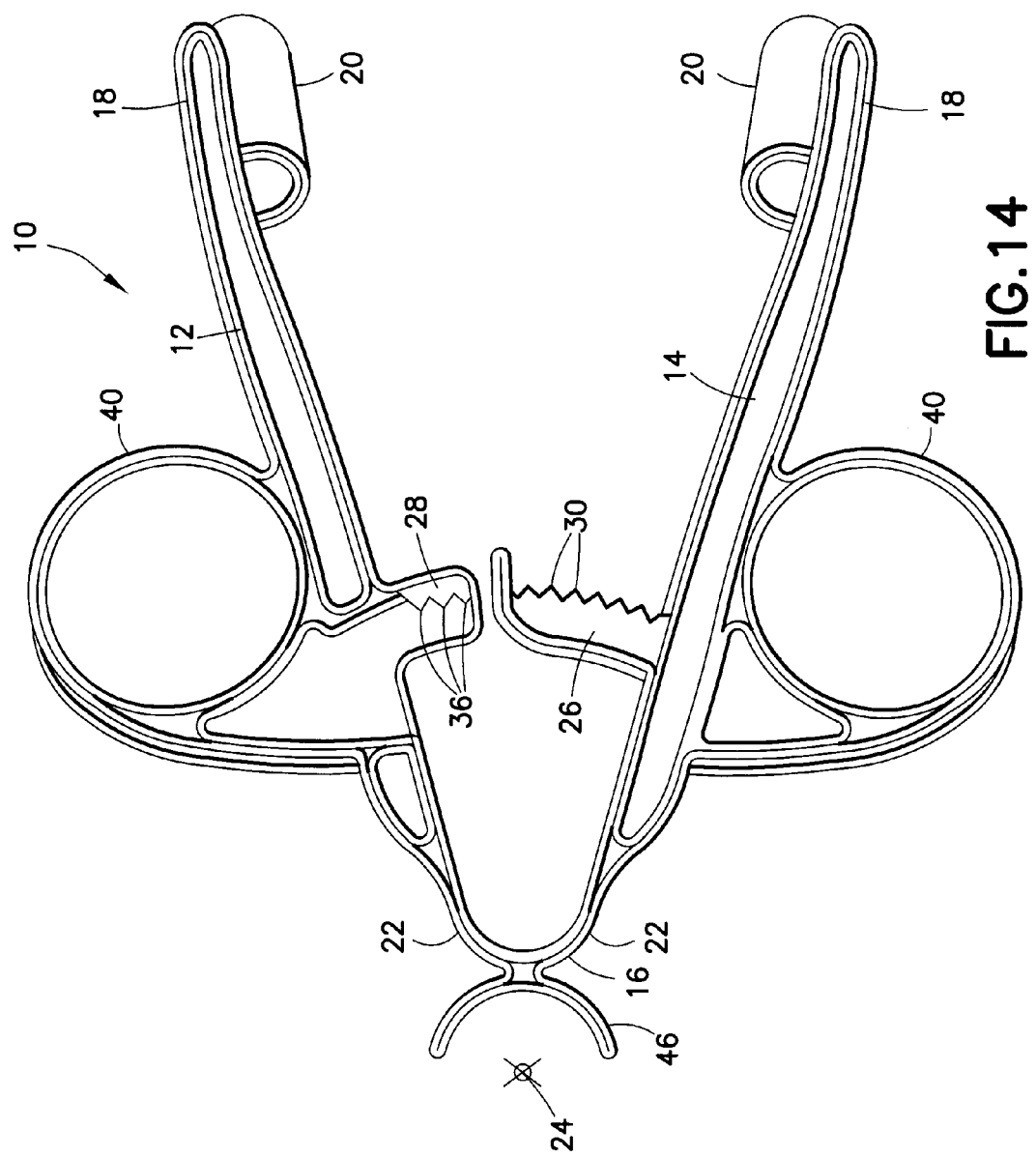
Figure 15:
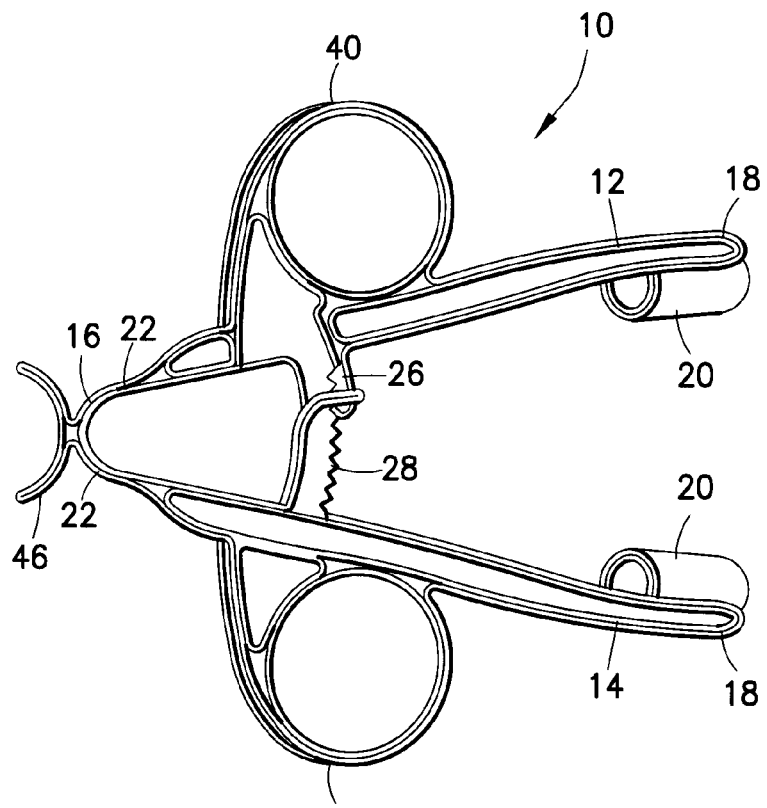
Figure 16:
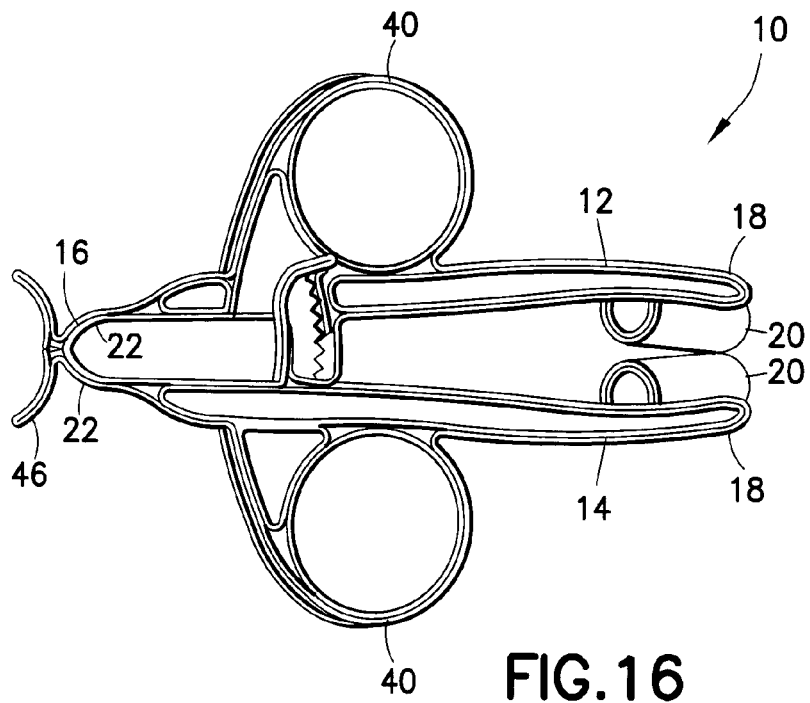

It is preferred that the speculum 10 be provided with a position retaining arrangement, whereby the first and second arms 12, 14 may be retained in a particular relative position. With reference to FIGS. 8 and 9, complementary first and second elements 26, 28 are unitarily formed on the first and second arms 12, 14, respectively. In particular, the first element 26 preferably includes a series of teeth 30, each defining a peak 32. By way of non-limiting example, the teeth 30 may be saw-tooth shaped, but other shapes are possible. Recesses 34 are defined between adjacent pairs of the teeth 30. The second element 28 preferably includes a pointer 36 formed to nest within the recesses 34 between the peaks 32 of adjacent pairs of the teeth 30. Two or more of the pointers 36 may be also arranged in series to engage the teeth 30, as shown in FIGS. 14-16. As will be appreciated by those skilled in the art, the first and second elements 26, 28 may be reversibly located on the front and second arms 12, 14.

Preferably, the teeth 30 are configured to by-pass the pointer 36 over a predetermined range of relative movement between the first and second arms 12, 14. The pointer 36 is formed to restrict movement of the teeth 30 relative thereto.

As shown in FIG. 8, in a preferred embodiment, a pair of the set of teeth 30 is provided with a channel 38 therebetween. The channel 38 permits the teeth 30, particularly the two sets of the teeth 30, to straddle a portion of the second arm 14, in providing stability during interengagement of the corresponding elements. In addition, a pair of the pointers 36 may be utilized.

With reference to FIGS. 1 and 2, in the initial pre-use state, the first and second elements 26, 28 are preferably separated and out of contact. The speculum 10 is maintained in the pre-use state, as shown in FIG. 2, through inherent memory provided to the speculum 10 during manufacturing.

During use, and with initial coming together of the proximal ends 22 of the first and second arms 12, 14, resulting in separation of the distal ends 18, the first element 26 is caused to engage the second element 28, particularly with the teeth 30 by-passing the pointer 36. The pointer 36 imparts resistance against further separation of the distal ends 18 due to interfering interengagement with the teeth 30. A threshold amount of force allows such resistance to be overcome to permit adjustment of the teeth 30 relative to the pointer 26.

With the pointer 36 nesting between adjacent pairs of the teeth 30, the relative positions of the first and second arms 12, 14 may be adjusted and maintained as needed. Thus, the states shown in FIGS. 6 and 7, adjusted from the pre-use state of FIG. 2, may be achieved and maintained.

The speculum 10 is used to open the eyelids of a patient and to maintain that open state. The degree to which the eyelids are opened may be adjusted as described above. It is noted that the eyelids may impart a reactionary closing force against the speculum 10. The threshold level of resistance against relative movement generated by the first and second elements 26, 28 must be greater than the closing force applied by the eyelids.

With a procedure being completed, force is applied to separate the proximal ends 22 of the first and second arms 12, 14, with sufficient force being applied to permit reverse relative movement of the teeth 30 past the pointer 36 to return the speculum 10 to a state permitting the channels 22 to be removed from a patient's eyelids. The speculum 10 is intended for single use.

Figure 3:
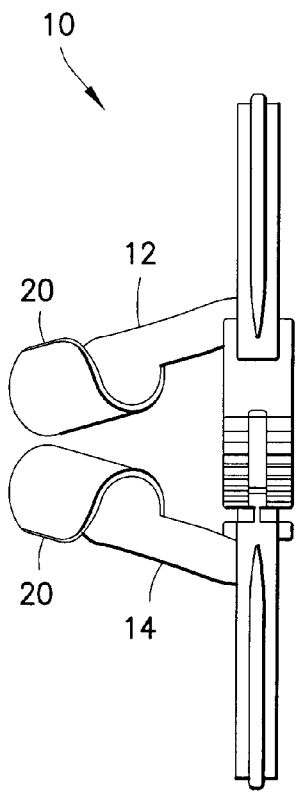
Figure 4:
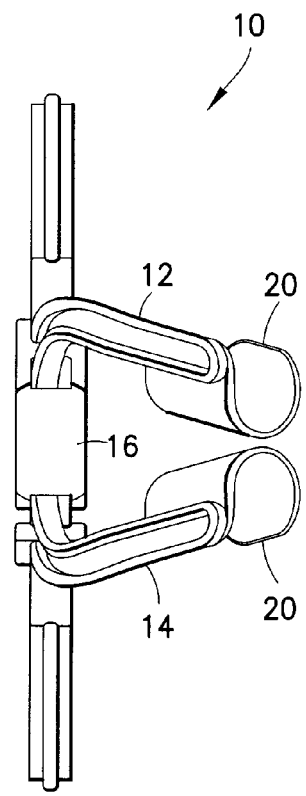
Figure 5:
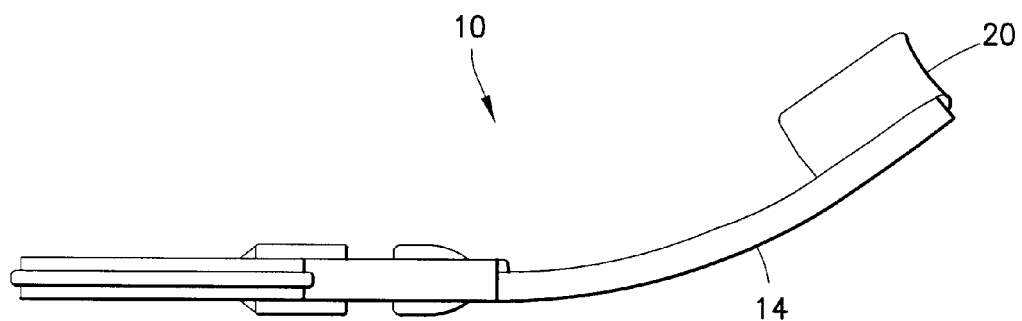

The speculum 10 may be formed with additional features, such as with the first and second arms 12, 14 being curved, as shown in FIGS. 3-5. Preferably, the portions of the first and second arms 12, 14 between the hinge 16 and the distal ends 18 are curved away from a plane which intersects the proximal ends 22 and the hinge 16. The curved configuration permits placement of the speculum 10 during use adjacent to the eye and without interference of the curvature of a person's face. In addition, finger holes 40 may be formed at the proximal ends 22 to provide easier manipulation of the first and second arms 12, 14 for use.

As will be appreciated by those skilled in the art, the hinge 16 is preferably a living hinge and may be formed with various configurations. With reference to FIGS. 1-7, the hinge 16 may be formed as a strip of relatively uniform thickness. With reference to FIGS. 10-13, the hinge 16 is preferably formed with thinned section 42 which permits easier rotation thereabout. The thinned section 42 provides greater predictability in operation of the hinge 16. More than one of the thinned sections 42 may be utilized. In addition, one or more ribs 44 may be provided about one or more of the thinned sections 42 so as to add additional rigidity to the hinge 16.

The speculum 10 can be also provided with hard stops limiting the extent of relative movement between the first and second arms 12, 14. Preferably, as shown in FIGS. 26-29, one or more stop blocks 41 may be provided to limit the movement of the first and second arms 12, 14, particularly to prevent the distal ends 18 from contacting. With the configuration of FIG. 2, the stop blocks 41 may be located distally of the hinge 16 and shaped to come into interfering engagement with a predetermined extent of movement of the distal ends 18 coming together. The stop blocks 41 may extend from the first arm 12, the second arm 14 and/or the hinge 16. The stop blocks 41 may be wedge-shaped to come into contact over a limited region 43. Due to the interfering engagement, contact between the distal ends 18 may be avoided and, as such, interference therebetween may be avoided. With reference to FIG. 2, portions of the distal end 18, for example at the channels 20, may come together to limit the extent of movement of the distal ends 18 coming together. In addition, with reference to FIG. 7, the proximal ends 22 of the first and second arms 12, 14, may be configured to come into contact to limit the extent to which the distal ends 18 may be separated.

Figure 17:
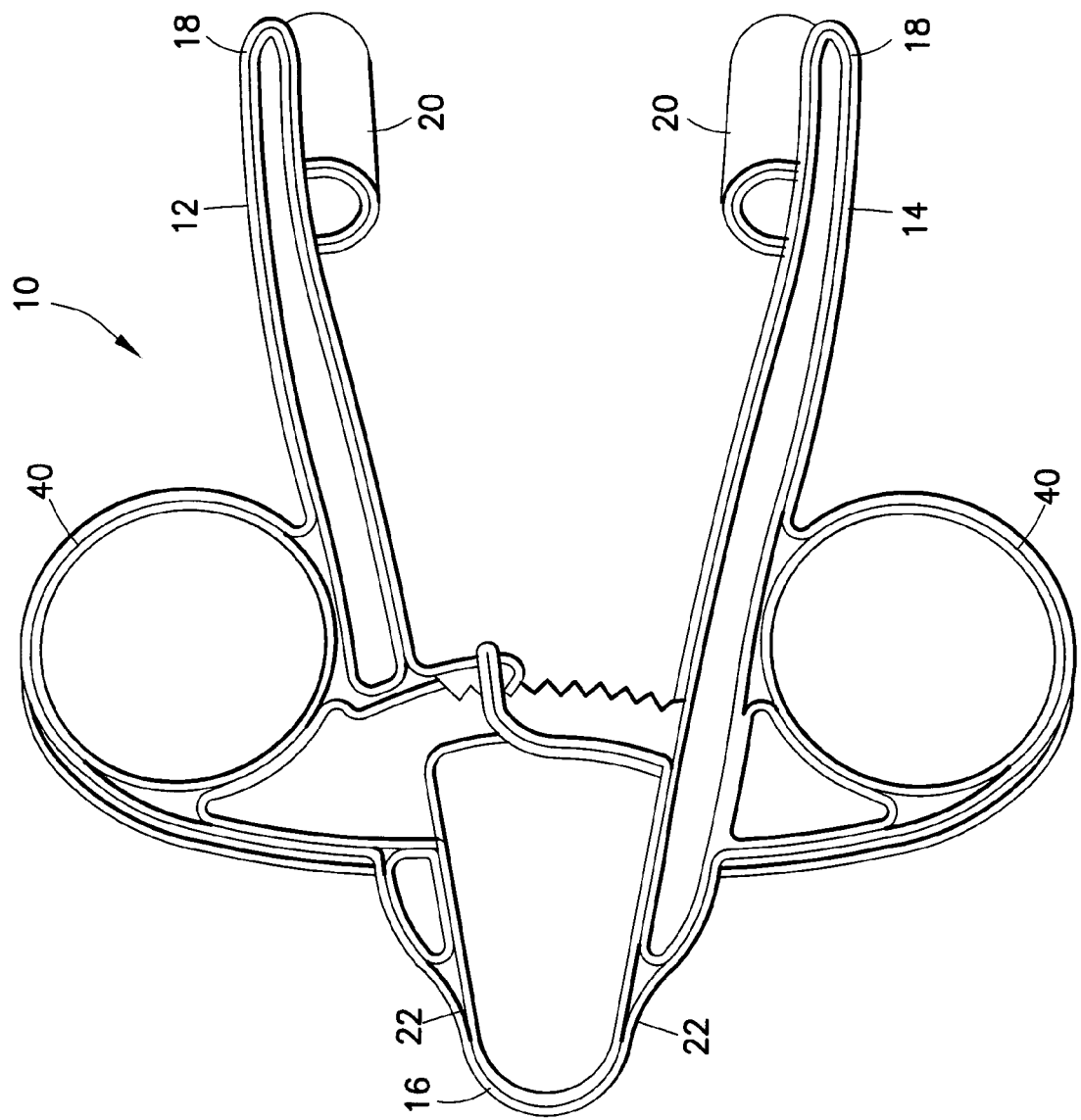

With reference to FIGS. 14-18, the hinge 16 may be located at the proximal ends 22 of the first and second arms 12, 14 (opposite ends of the first and second arms 12, 14 from the channels 20 thereof). With this arrangement, the finger holes 40 may be located at mid-points on the first and second arms 12, 14 between the distal and proximal ends 18, 22. With the hinge 16 being located at the proximal ends 22, the distal ends 18 are caused to move apart by separating the first and second arms 12, 14 and, conversely, brought closer together by bringing the first and second arms 12, 14 together. As shown in FIGS. 14-16, a side support 46 may be provided extending from the hinge 16. The side support 46 defines a resting surface for a third finger of a user during operation. Thus, with the configuration of FIGS. 14-16, a user may place a thumb and a forefinger in the finger holes 40 with a ring finger or pinkie being pressed against the side support 46 for additional stability. As shown in FIG. 17, the side support 46 need not be provided.

Figure 18:
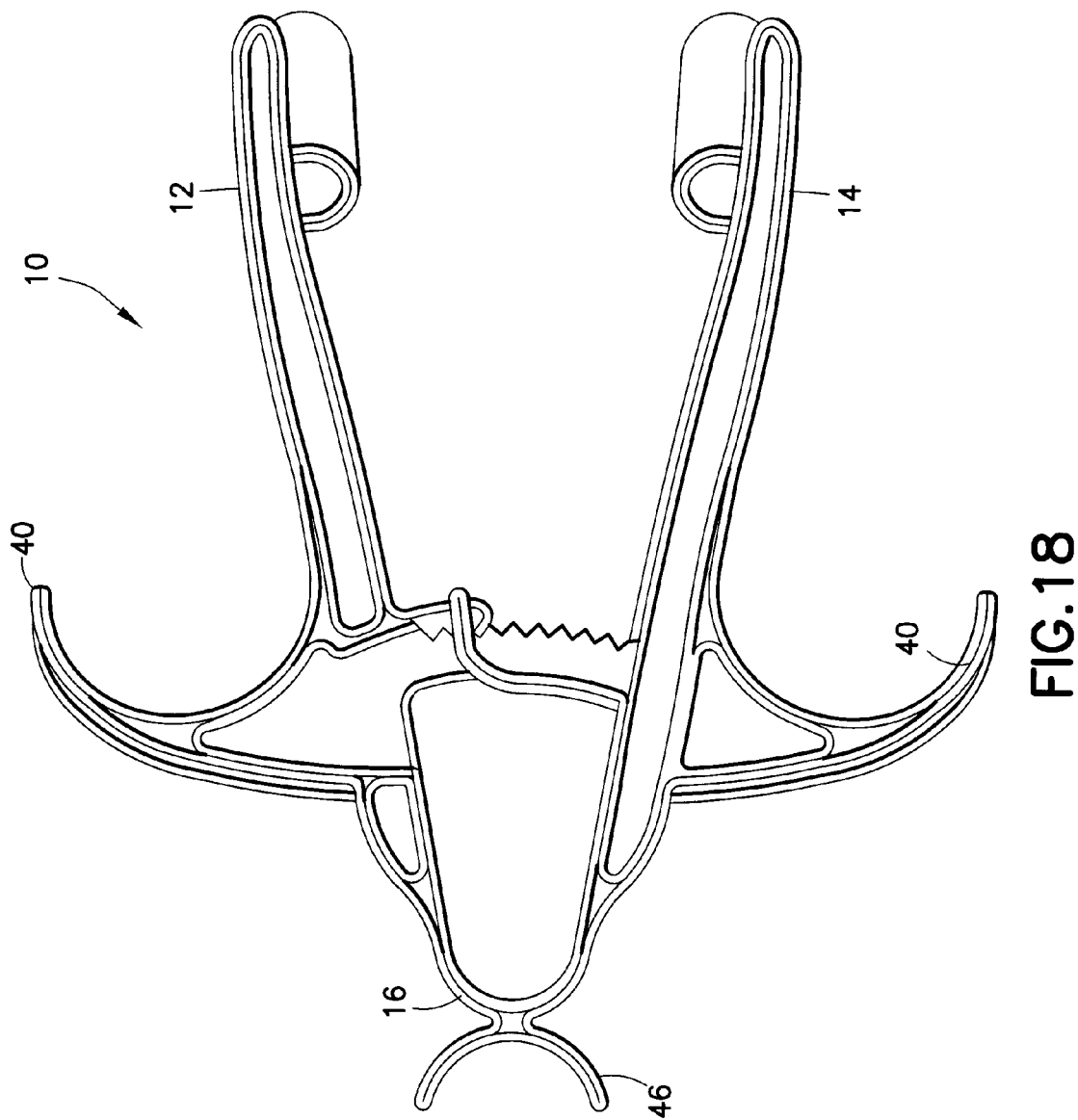
Figure 19:
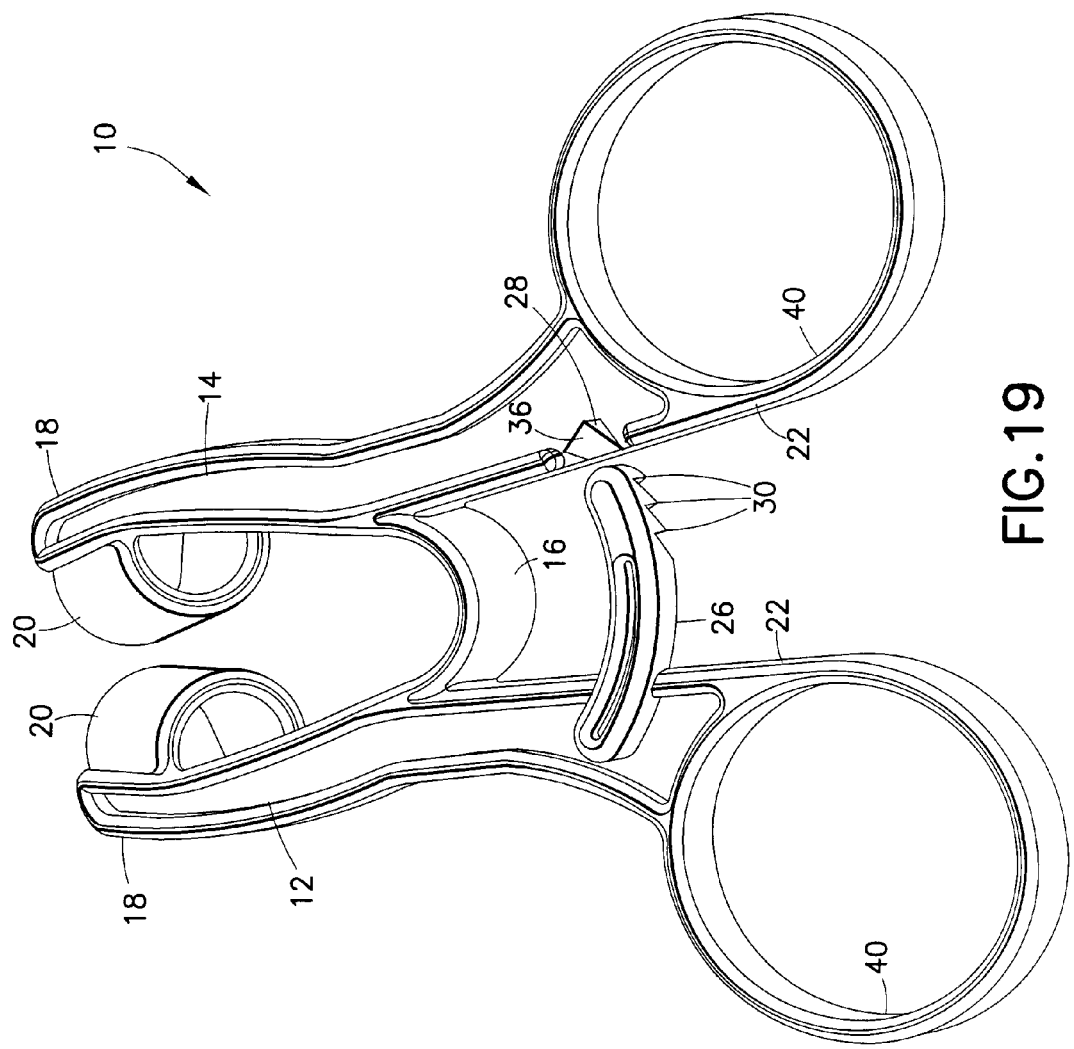
Figure 20:
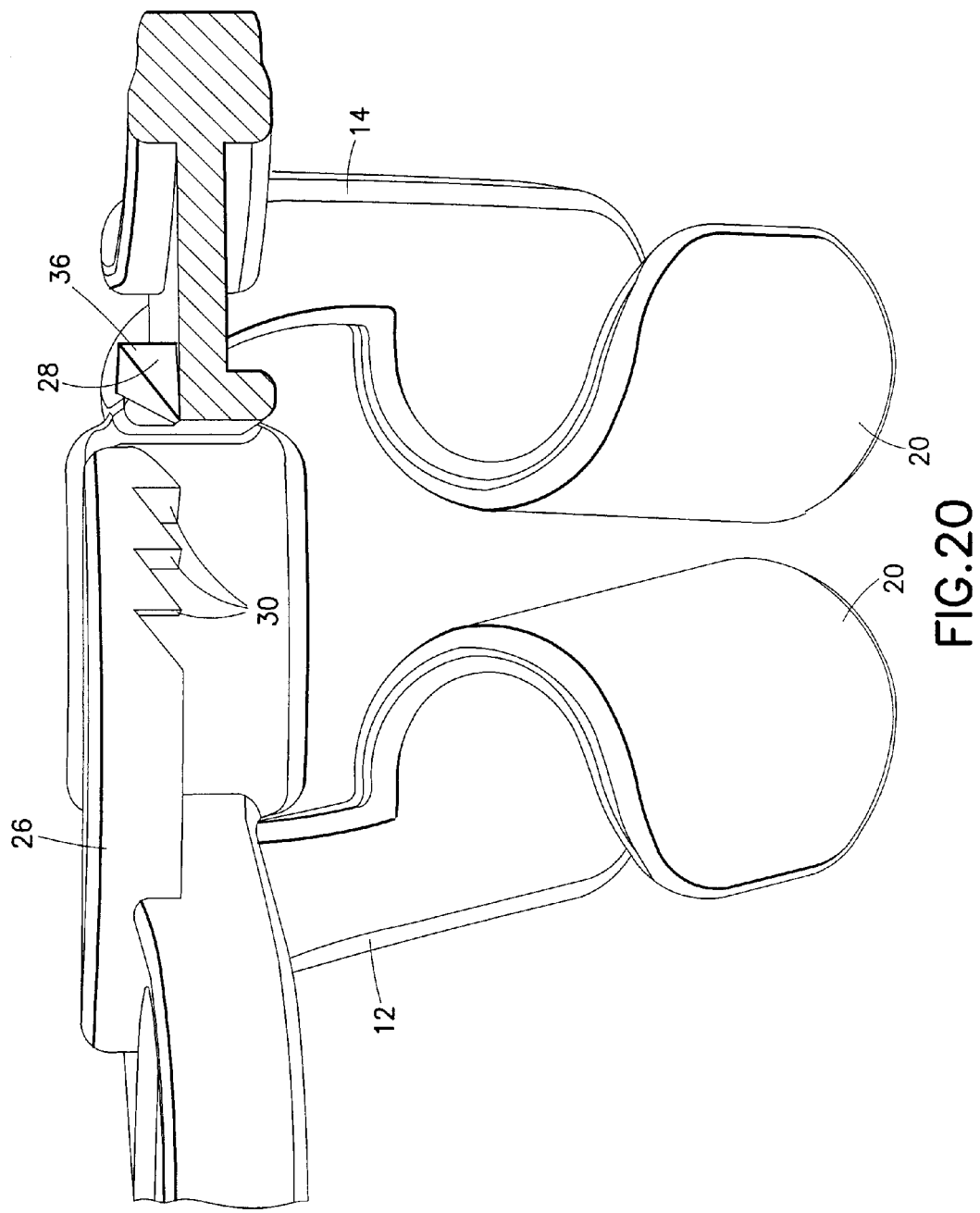
Figure 21:
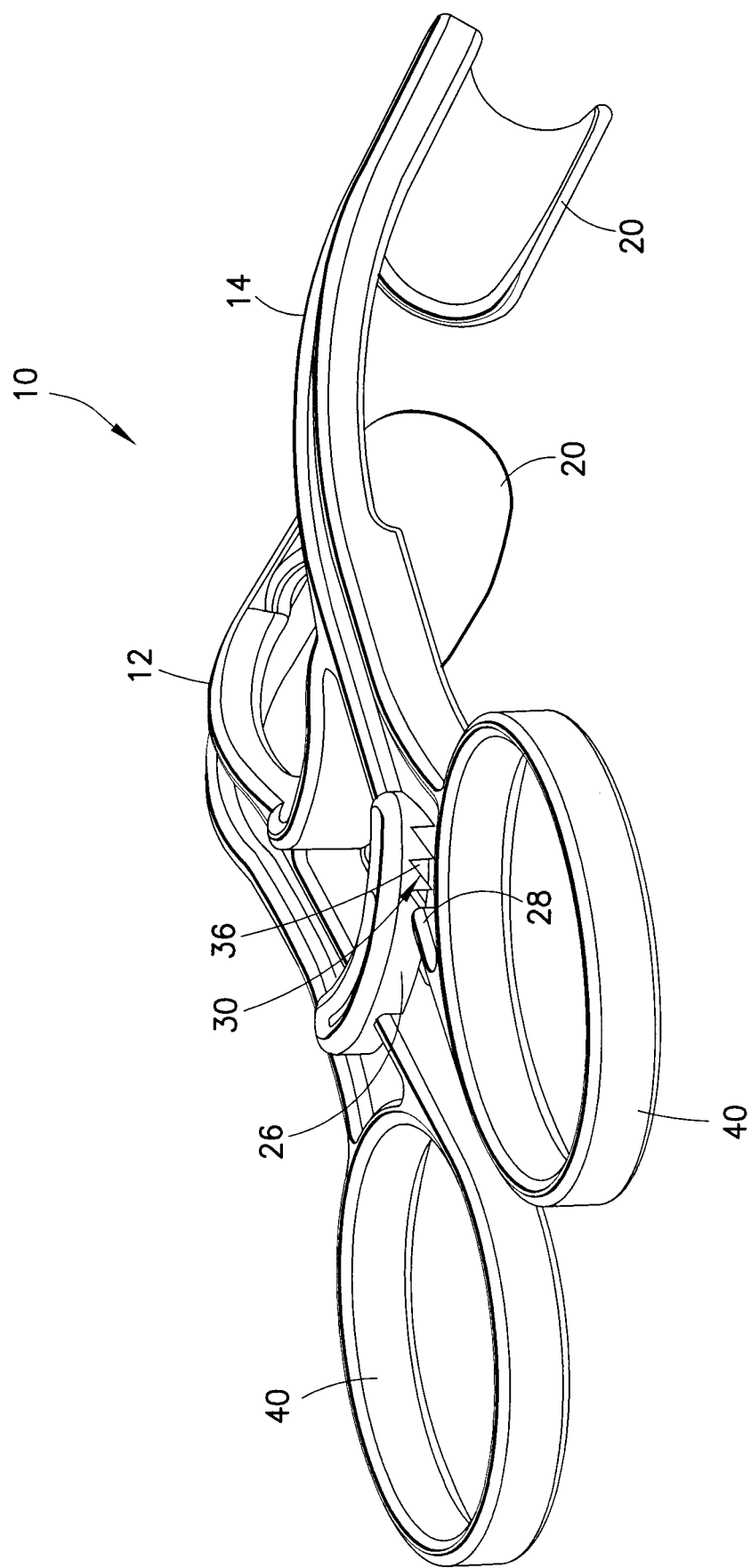

With respect to FIG. 18, it is noted that the finger holes 40 may be defined by a partial loop, as opposed to the complete loop shown, for example, in FIGS. 1-7. It is preferred that the finger holes 40 have sufficient definition to accept and transmit force for both opening and closing the speculum 10.

Figure 22:
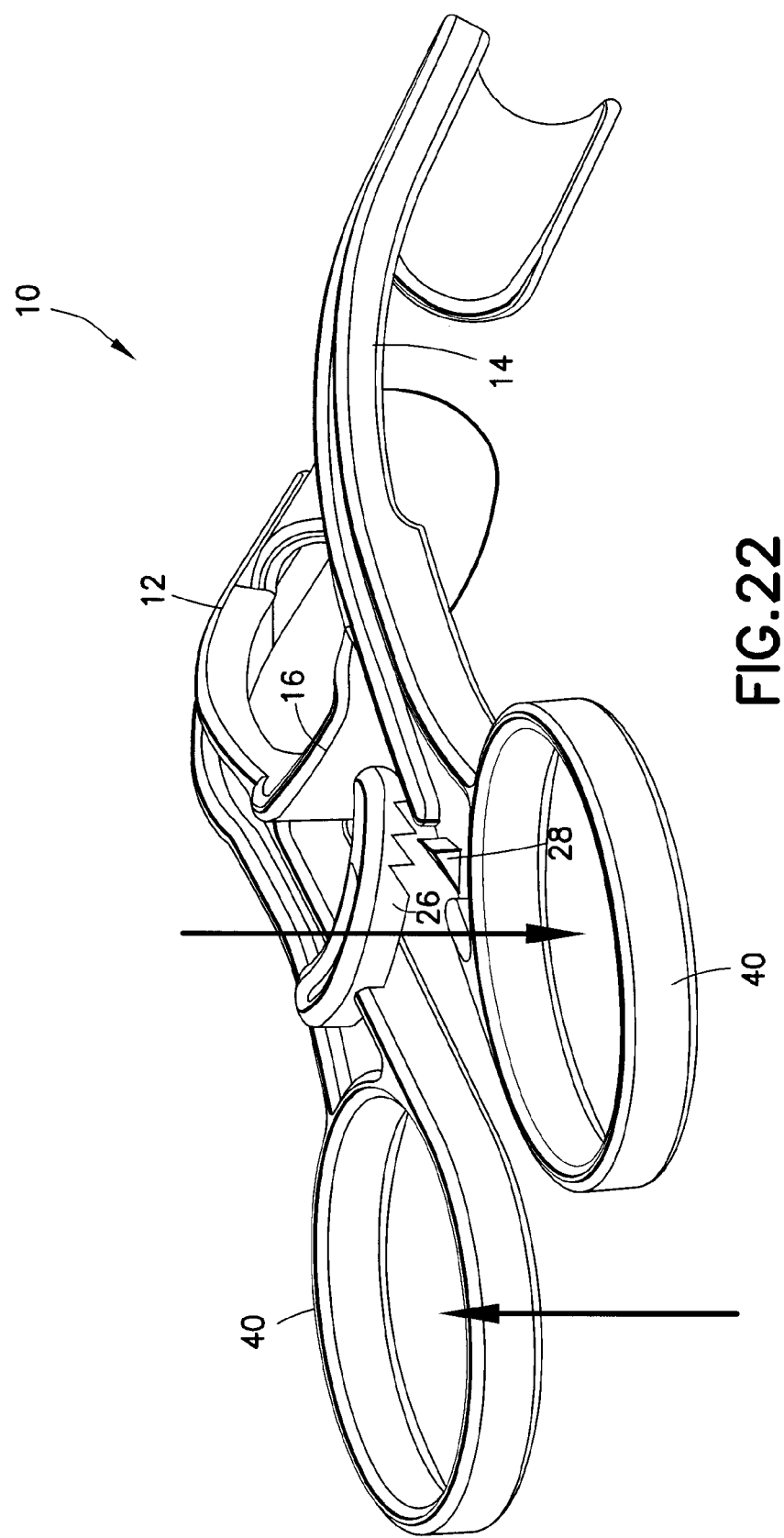
Figure 23:
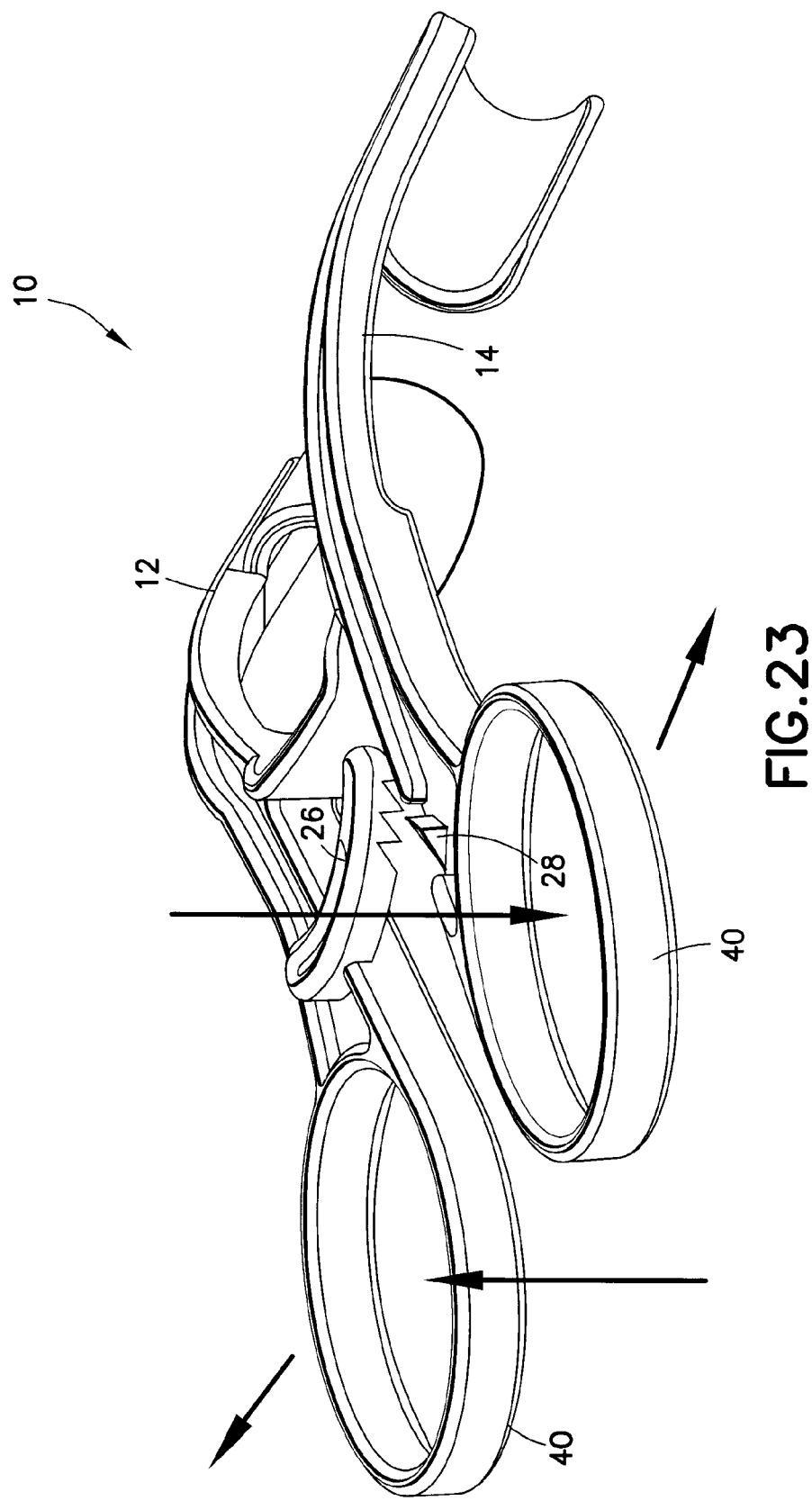
Figure 24:
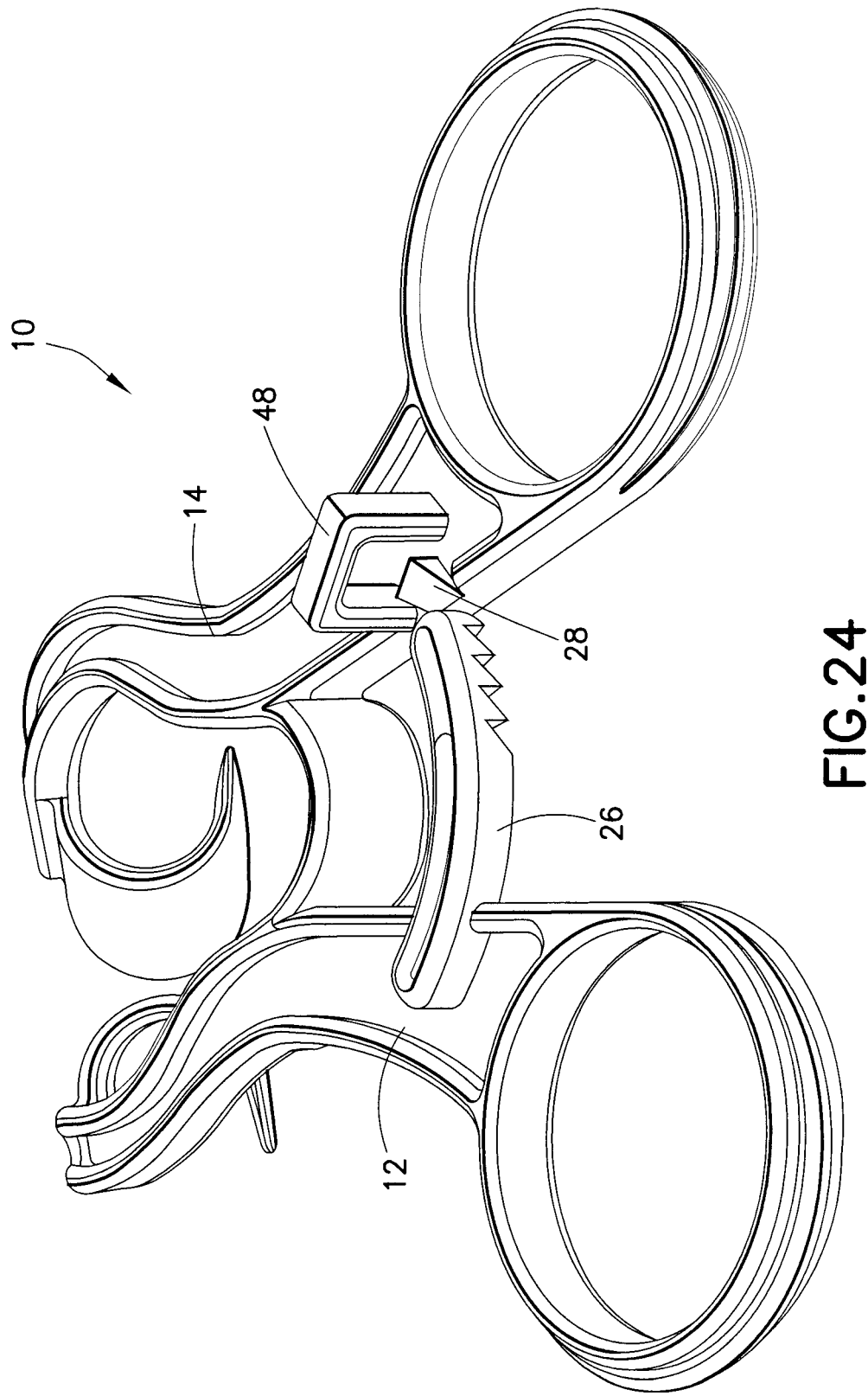
Figure 25:
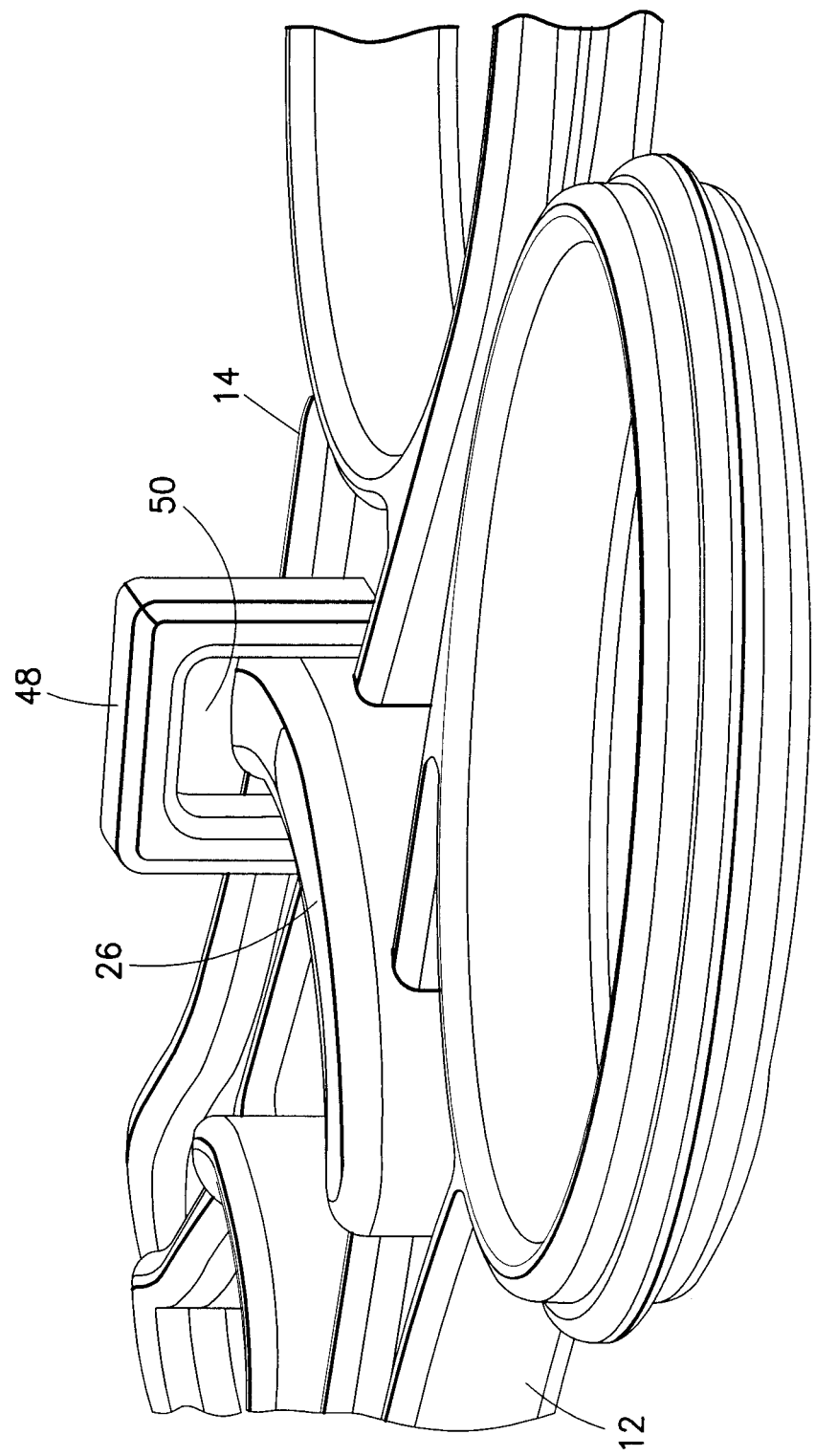
Figure 26:
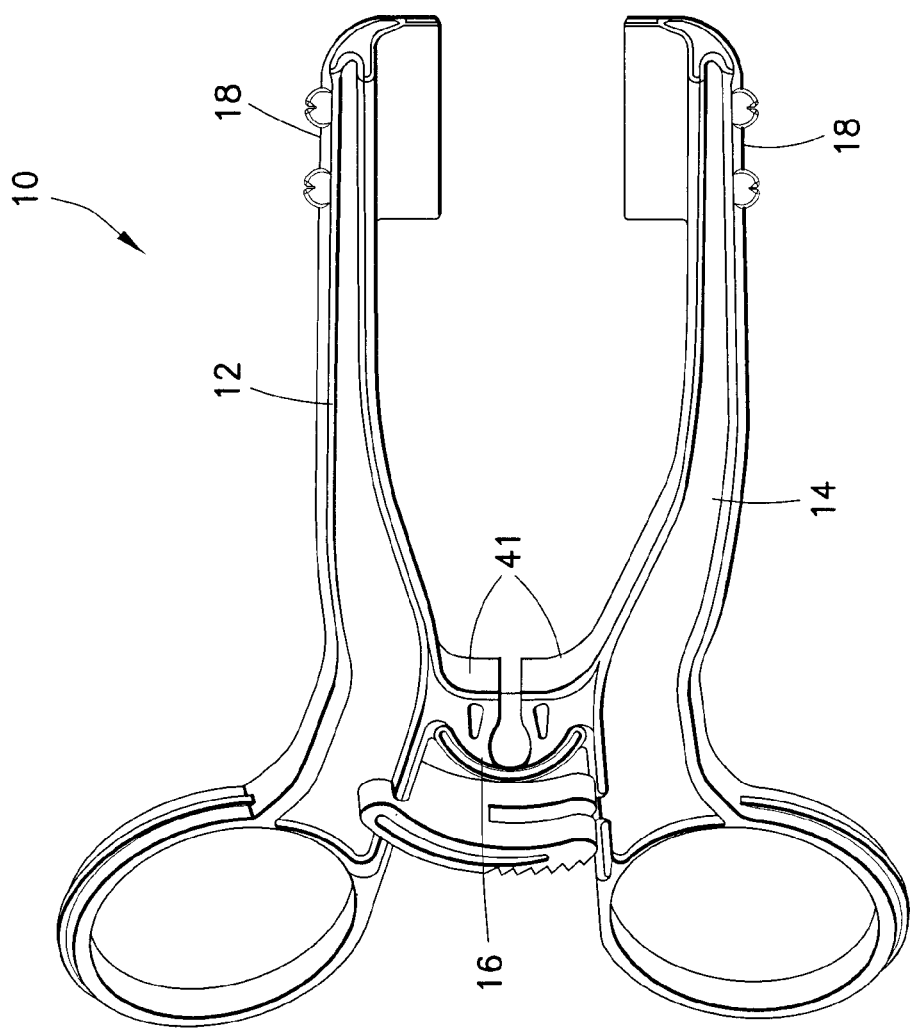
Figure 27:
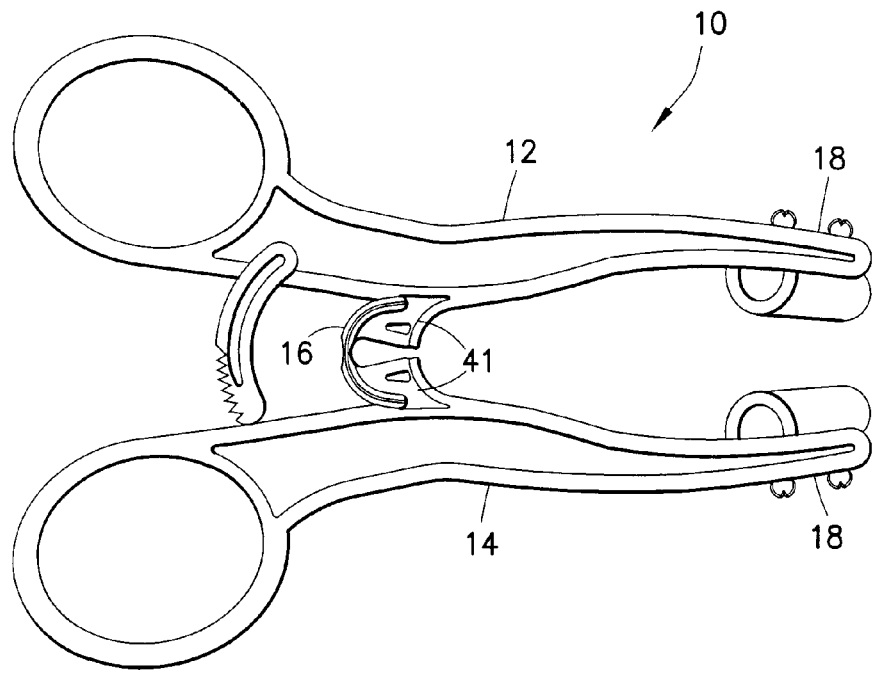
Figure 28:
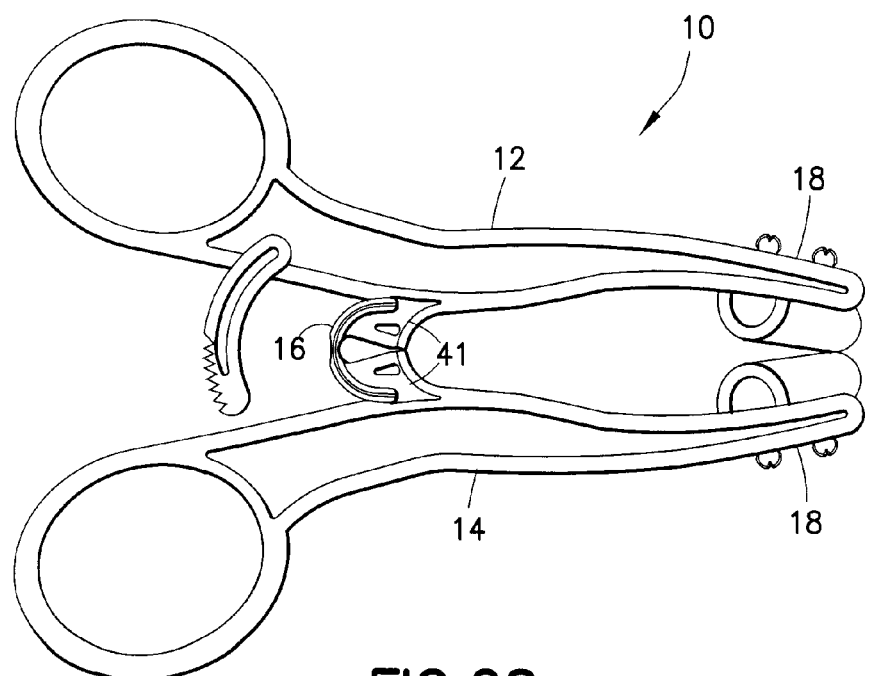
Figure 29:
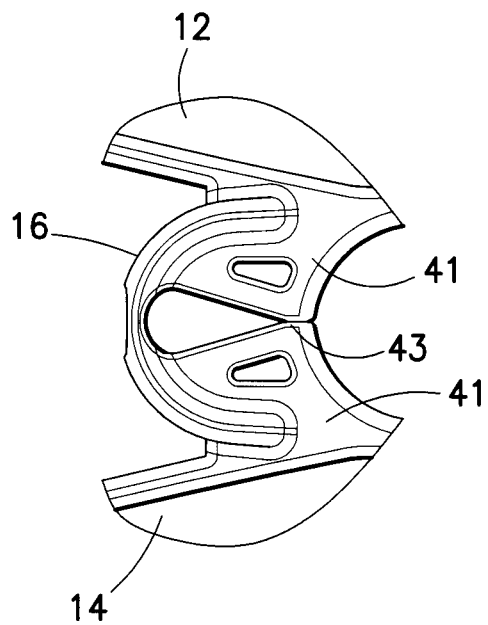
Figure 30:
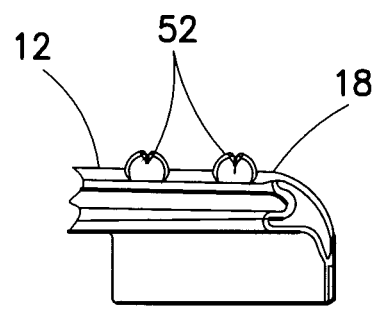
Figure 31:
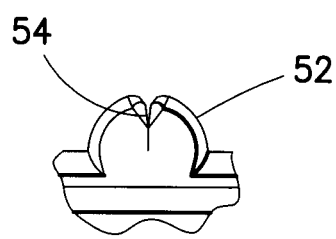
Figure 32:
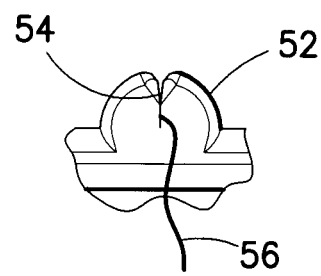
Figure 33:
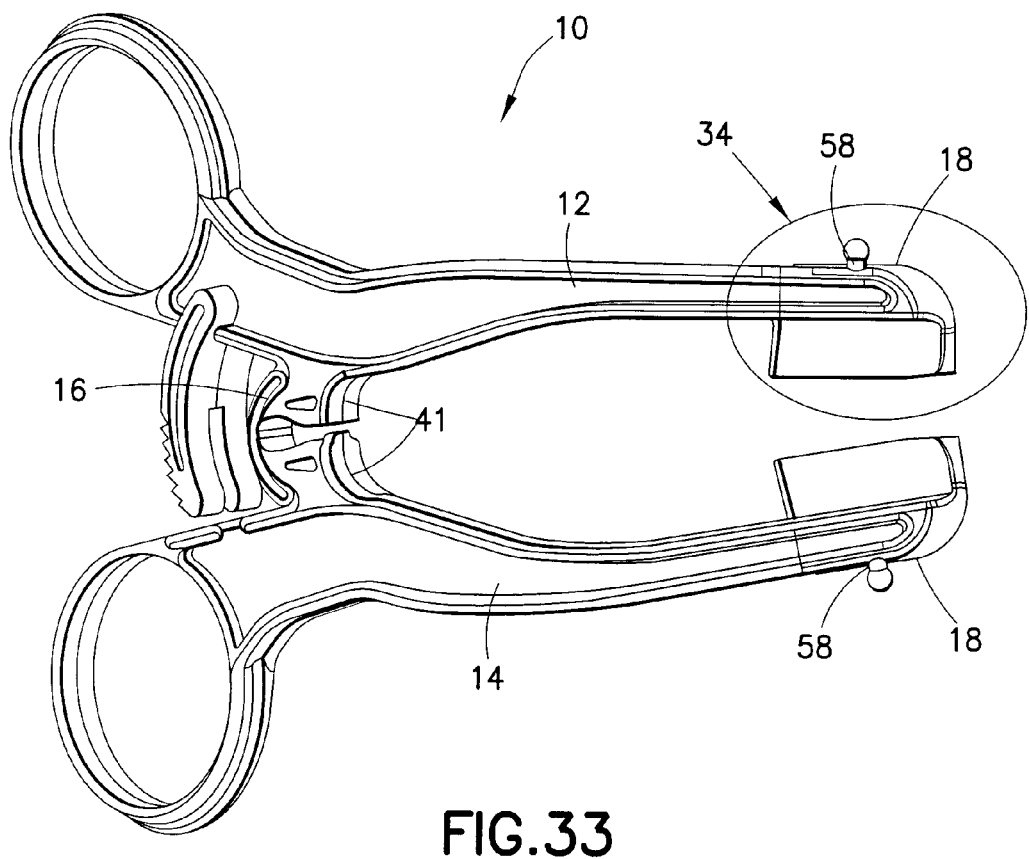
Figure 34:
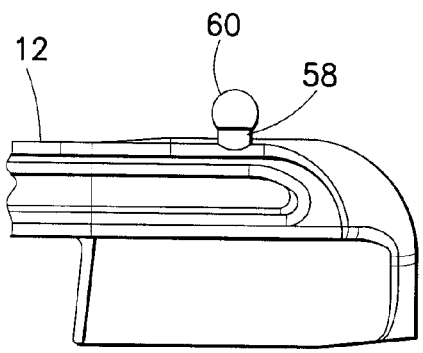
Figure 35:
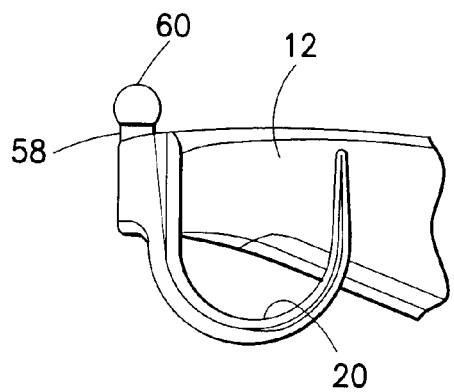

It is also noted that the first and second elements 26, 28 in the embodiments discussed above, are orientated to have the teeth 30 and the pointer 36 extend in a direction generally parallel to the longitudinal axes of the first and second arms 12, 14. With reference to FIGS. 19-23, the teeth 30 and the pointer 36 may be oriented in a direction generally perpendicular to the longitudinal axes of the first and second arms 12, 14. With this arrangement, as shown in FIGS. 22 and 23, the first and second arms 12, 14 may be positionally adjusted by applying a torsional force about the hinge 16 to separate the first and second elements 26, 28. Once separated, the first and second arms 12, 14 are free to be positionally adjusted. Once in a desired position, the torsional force is removed so as to permit re-interengagement of the first and second elements 26, 28 to provide a retaining force in the same manner as described above. The inherent memory of the speculum 10 causes the first and second arms 12, 14 to return to an unbiased state where the first and second elements 26, 28 interengage. As shown in FIGS. 24-25, an arch-shaped bridge 48 may be provided to limit the extent of separation of the first and second elements 26, 28. As shown in FIGS. 24-25, the bridge 48 may be formed on the second arm 14 with an opening 50 sized to permit passage therethrough of the first element 26. The opening 50 is sized to permit sufficient separation of the first and second elements 26, 28 to permit positional adjustment of the first and second arms 12, 14, yet limits excessive separation.

Alternatively, as shown in FIG. 17A, the first and second elements 26, 28 may be separated axially by displacing one or both of the first and second arms 12, 14. In a separated state, the first and second arms 12, 14 may be positionally adjusted. It is preferred that the hinge 16 be located at the proximal ends 22 of the first and second arms 12, 14 for this arrangement.

As a further variation, and with reference to FIGS. 26-35, one or more features for retaining sutures may be provided. For example, with reference to FIGS. 26-32, one or more suture cleats 52 may be located on the first arm 12 and/or the second arm 14, preferably in proximity to the distal end(s) 18. The suture cleats 52 each include a notch 54 formed to resiliently grip a thread or suture 56 therein. Preferably, a sufficiently strong resilient grip is generated by each of the cleats 52 in the notch 54 to retain the suture 56 therein without movement of the suture 56 relative to the first and second arms 12, 14 during movement of the first and second arms 12, 14. The resilient grip is generated by the inherent resilience of portions of the cleats 52 surrounding the notch 54. Preferably, and with reference to FIGS. 33-35, one or more suture posts 58 may be provided about which sutures can be wrapped and tied off. To minimize inadvertent slippage, an enlarged head 60 may be provided on each of the suture posts 58 which limits slippage of a suture from the suture post 58. The suture posts 58 may be easier to manufacture with the speculum 10 than the suture cleats 52, e.g., by injection molding.

As will be appreciated by those skilled in the art, the various features discussed herein may be used in various combinations with the speculum 10. In any regard, it is preferred that the speculum 10 be formed as a single, unitary piece. Preferably, the speculum 10 is formed of a moldable thermoplastic material, which is sterilizeable. In this manner, the speculum 10 can be molded as a single piece in various molding techniques, such as injection molding. It is also preferred that the material of the speculum 10 not be capable of withstanding autoclaving. By not being capable of withstanding autoclaving, the likelihood of re-using the speculum 10 is greatly reduced. This minimizes potentially unsafe re-use. In initial manufacturing, it is preferred that the speculum 10 be prepared with gamma radiation or gas (e.g., EtO) sterilization. Advantageously, the speculum 10 can be provided as a one-piece article, which requires beyond initial molding no additional manufacturing or assembly steps, and which is single-use, which limits improper and potentially unsafe re-use.

What is claimed is:

1. A speculum comprising:
   a first arm having a trough-shaped first channel formed thereon, said first channel having an open portion adapted to the shape of an eyelid;
   a second arm having a trough-shaped second channel formed thereon, said second channel having an open portion adapted to the shape of an eyelid, said open portion of said second channel facing away from said open portion of said first channel;
   a hinge unitarily formed with said first and second arms, said hinge permitting said first and second arms to selectively rotate about an axis of rotation, said selective rotation causing said first and second channels to selectively move closer and farther apart; and,
   a position retaining arrangement including:
   at least two first elements formed unitarily with said first arm, said first elements being spaced apart in a direction parallel to said axis of rotation so as to define a channel therebetween; and,
   a second element formed unitarily with said second arm;
   wherein, said first and second elements being configured to cooperatively retain said first and second arms in a selected rotational position,
   wherein, with said first and second elements being in cooperative retention, said first elements straddle said second arm with a portion of said second arm received in said channel, and,
   wherein the speculum is monolithically formed as one piece.

2. A speculum as in claim 1, wherein said first and second elements are configured to interferingly interengage so as to limit rotational movement of said first and second arms.

3. A speculum as in claim 2, wherein said first and second elements are separable to permit rotation of said first and second arms.

4. A speculum as in claim 2, wherein a predetermined amount of force may be applied to cause selective rotation of said first and second arms, said predetermined amount of force being sufficient to overcome a retaining force generated by said first and second elements.

5. A speculum as in claim 1, wherein said first arm includes a finger hole.

6. A speculum as in claim 1, wherein the speculum is formed of thermoplastic.

7. A speculum as in claim 1, wherein said hinge is located along a mid-point of said first and second arms.

8. A speculum as in claim 1, wherein, in an initial state, said first and second channels are in proximity.

9. A speculum as in claim 1, wherein, in an initial state, said first and second elements are separated and out of contact.

10. A speculum as in claim 1, further comprising stop blocks configured to limit the extent of rotation of said first and second arms.

11. A speculum as in claim 1, wherein said hinge is located on said first and second arms at opposite ends from said channels thereof.

12. A speculum as in claim 1, further comprising one or more features for retaining sutures.

13. A speculum comprising:
    a first arm having a trough-shaped first channel formed thereon, said first channel having an open portion adapted to the shape of an eyelid;
    a second arm having a trough-shaped second channel formed thereon, said second channel having an open portion adapted to the shape of an eyelid, said open portion of said second channel facing away from said open portion of said first channel;
    a hinge connected to said first and second arms, said hinge permitting said first and second arms to selectively rotate about an axis of rotation, said selective rotation causing said first and second channels to selectively move closer and farther apart;
    at least two first elements on said first arm, said first elements being spaced apart in a direction parallel to said axis of rotation so as to define a channel therebetween; and,
    a second element on said second arm;
    wherein, said first and second elements are configured to cooperatively retain said first and second arms in a rotational position with interfering interengagement between said first and second elements limiting rotation of said first and second arms, wherein, with said first and second elements being in cooperative retention, said first elements straddle said second arm with a portion of said second arm received in said channel, and wherein the speculum is monolithically formed as one piece.

14. A speculum as in claim 1, wherein said hinge is a living hinge.

15. A speculum as in claim 13, wherein said hinge is a living hinge.

16. A speculum as in claim 1, wherein the speculum is monolithically formed by molding as one piece.

17. A speculum as in claim 13, wherein the speculum is monolithically formed by molding as one piece.

* * * * *